United States Patent [19]
Nakata et al.

[11] Patent Number: 6,040,343
[45] Date of Patent: Mar. 21, 2000

[54] REMEDY FOR KERATOCONJUNCTIVAL DISEASES

[75] Inventors: Katsuhiko Nakata, Sakurai; Masatsugu Nakamura, Nara; Takashi Hamano, Ashiya, all of Japan

[73] Assignee: Santen Pharmaceutical Co., Ltd., Osaka, Japan

[21] Appl. No.: 09/101,110

[22] PCT Filed: Jan. 17, 1997

[86] PCT No.: PCT/JP97/00081

§ 371 Date: Jul. 17, 1998

§ 102(e) Date: Jul. 17, 1998

[87] PCT Pub. No.: WO97/26872

PCT Pub. Date: Jul. 31, 1997

[30] Foreign Application Priority Data

Jan. 22, 1996 [JP] Japan ..................................... 8-008243

[51] Int. Cl.$^7$ ........................... A61K 31/22; A61K 31/23
[52] U.S. Cl. ........................... 514/549; 514/552; 514/912; 560/205; 560/225
[58] Field of Search .................................. 514/549, 552, 514/912, 915, 925; 560/205, 225

[56] References Cited

FOREIGN PATENT DOCUMENTS 39-28230  12/1964  Japan .
6-192073  7/1994  Japan .

OTHER PUBLICATIONS

Fukada et al, "Dry Eye and Corneal and Conjunctival Epithelium", Journal of the Eye, 8, pp. 1037–1042 (1991) and partial English language translation.

Slomiany et al, "Effect of Ebrotidine on the Synthesis and Secretion of Gastric Sulfomucin", Gen. Pharmac., 24, pp. 611–617 (1993).

Watanabe, "Effect Of Methylmethionine Sulfonium Chloride (MMSC) On Gastric Mucin In Relation With Ethanol–Induced Injury in Rats", Jpn. Pharmacol. Ther., 22, pp. 4355–4361 (1994) and partial English language translation.

Shigemoto et al, "Mucosal Protective Drug", Pharma Medica, 4, pp. 45–48 (1986) and partial English language translation.

J. Bilski et al, "Enhancement of the Lipid Content and Physical Properties of Gastric Mucus by Geranylgeranyl-lacetone", Biochemical Pharmacology, vol. 36, No. 23, pp. 4059–4065, 1987.

*Primary Examiner*—Howard C. Lee
*Attorney, Agent, or Firm*—Frishauf, Holtz, Goodman, Langer & Chick, P.C.

[57] ABSTRACT

The present invention provides a novel substance which promotes the production and secretion of mucin in ophthalmic tissues.

The therapeutic agent for keratoconjunctiva diseases according to the present invention contains gefarnate as an active ingredient. This therapeutic agent for keratoconjunctiva diseases is applicable to dry eye, keratitis, conjunctivitis, corneal erosion, corneal ulcer, etc. The dosage form is preferably an ophthalmic solution. Concentration of gefarnate is, for example, 0.1–3% (w/v).

14 Claims, No Drawings

REMEDY FOR KERATOCONJUNCTIVAL DISEASES

TECHNICAL FIELD

The present invention relates to a therapeutic agent for keratoconjunctiva diseases containing gefarnate as an active ingredient.

BACKGROUND ART

In general, organisms directly contact the outside demarcated by mucous surface of digestive tracts, respiratory organs, etc. and are always exposed to the danger of invasion of microbes and foreign substances from outside. Therefore, organisms are equipped with a defense mechanism for protecting the mucous membrane. That is to say, although mucous membrane is covered with only a single layer of mucoepithelium, the epithelial cells are always covered with a viscous exocrine liquid containing mucin secreted from exocrine gland and the exocrine liquid prevents microbes and foreign substances from contacting the epithelial cells directly. In eyes, tear plays such a role and wets the surface of the eye balls.

Tear layer consists of three layers, that are oily layer, aqueous layer and mucus layer, and keratoconjunctiva epithelial cells are adjacent to the mucus layer. Mucin, which constitutes the mucus layer, is a glycoprotein mainly secreted from goblet cells of conjunctiva. It was known that mucin layer covers the surface of the hydrophobic keratoconjunctiva epithelial cells and change the property to hydrophilic ones to assist the maintenance and expansion of aqueous layer in tear whereby it plays an important role in keeping the normal structure of tear (*Journal of the Eye*, 8, 1037–1042(1991)).

Accordingly, if there is any substance having an action of promoting the secretion of mucin into tear fluid, it is expected that such a substance is useful to keratoconjunctiva diseases having a trouble on keratoconjunctiva epithelium such as dry eye, keratitis, conjunctivitis, corneal erosion and corneal ulcer.

Studies were made recently on the relation between drugs and production and secretion of mucin and it was reported that ebrotidine, which is a therapeutic agent for ulcer, promotes the production and secretion of rat gastric mucin (*Gen. Pharmac.*, 24, 611–617(1993)) and that participation of mucin is presumed in an antiulcerative action of methylmethionine sulfonium chloride (*Jpn. Pharmacol. Ther.*, 22, 4355–4361(1994)).

It was disclosed that gefarnate is a substance showing a strong antiulcerative action and is useful for therapy of peptic ulcers such as gastric ulcer and duodenal ulcer (Japanese Examined Patent Publication 28,230/1964). With regard to its function, it was reported that gefarnate promotes the deposition of acidic mucopolysaccharides on surface of a wound, to increase the amount of mucus such as hexosamine in gastric mucosa and is expected to protect the mucous membrane, etc. and to increase endogenous prostaglandins (*Pharma Med.*, 4, 45–48(1986)).

However, there has been no report on study in ophthalmologic field.

Although various studies have been made already for therapeutic agents for keratoconjunctiva diseases including dry eye, it is a very interesting theme to find new substances which promote the production and secretion of mucin in ophthalmic tissues.

DISCLOSURE OF THE INVENTION

The present inventors paid their attention to known drugs which have been used as therapeutic agents for ulcer from the viewpoint of protection of mucous membrane, studied their influence on production and secretion of mucin in ophthalmic tissues and observed that gefarnate promotes the production and secretion of mucin in keratoconjunctiva whereupon they have found that gefarnate is useful as a therapeutic agent for keratoconjunctiva diseases such as dry eye, keratitis, conjunctivitis, corneal erosion and corneal ulcer.

Although the details of influence of gefarnate on production and secretion of mucin in ophthalmic tissues will be mentioned under the paragraph of Pharmacological Tests, it has been found that gefarnate promotes the secretion of protein containing mucin by the study using sulfate ion which was labeled with radioisotope existing in corneal epithelium (hereinafter, the above-mentioned protein will be referred to as "mucin-containing protein"). It has been also found that, when the outermost layer of bulbar conjunctiva is collected and observed by means of impression cytology, gefarnate increases the number of goblet cells containing mucin in bulbar conjunctiva.

Examples of a dosage form of gefarnate are ophthalmic preparations such as ophthalmic solutions and opthalmic ointment and injections and gefarnate can be formulated into such preparations utilizing the widely-used method. In the case of ophthalmic solutions, for example, they can be prepared using isotonizing agents such as sodium chloride and concentrated glycerol; buffers such as sodium phosphate and sodium acetate; surfactants such as polyoxyethylene sorbitan monooleate (hereinafter, referred to as Polysolvate 80), stearic polyoxyl 40 and polyoxyethylene hydrogenated castor oil; stabilizers such as sodium citrate and sodium edetate; preservatives such as benzalkonium chloride and paraben; etc., if necessary. The pH can be within a range which is acceptable to ophthalmic preparations and, preferably within a range from 4 to 8.

The dose can be appropriately selected depending upon symptom, age, dosage form, etc. and, in the case of ophthalmic solutions, a solution of 0.01–5% (w/v), preferably 0.1–3%, is instilled once to several times daily. In the case of injection, 0.0001–5 mg, preferably 0.001–1 mg, per day can be administered once to several times a day.

BEST MODES FOR CARRYING OUT THE INVENTION

As hereunder, the results of the Formulation Examples and Pharmacological Tests are mentioned although they are given merely for better understanding of the present invention and are not intended for limiting the scope of the present invention.

FORMULATION EXAMPLES

Representative examples for preparing ophthalmic solutions and ophthalmic ointment of gefarnate are shown as follows.

1) Ophthalmic Solutions

| Formulation 1 (Preparation 1) (in 10 ml) | |
|---|---|
| Gefarnate | 10 mg |
| Sodium chloride | 90 mg |
| Polysolvate 80 | 50 mg |
| Sterile purified water | q.s. |

-continued

Formulation 2 (Preparation 2) (in 10 ml)

| | |
|---|---|
| Gefarnate | 30 mg |
| Sodium chloride | 90 mg |
| Polysolvate 80 | 50 mg |
| Sterile purified water | q.s. |

Formulation 3 (Preparation 3) (in 10 ml)

| | |
|---|---|
| Gefarnate | 100 mg |
| Sodium chloride | 90 mg |
| Polysolvate 80 | 50 mg |
| Sterile purified water | q.s. |

Formulation 4 (Preparation 4) (in 10 ml)

| | |
|---|---|
| Gefarnate | 300 mg |
| Sodium chloride | 90 mg |
| Polysolvate 80 | 50 mg |
| Sterile purified water | q.s. |

2) Ophthalmic Ointment:
Formulation 1 (Preparation 5) (in 100 g)

| | |
|---|---|
| Gefarnate | 1 g |
| Liquid paraffin | 10 g |
| White vaseline | 84 g |
| Purified lanolin | 5 g |

[Pharmacological Tests]

In order to investigate the usefulness of gefarnate, its influence on production and secretion of mucin in corneal epithelium and bulbar conjunctiva was studied.

1. Production and Secretion of Mucin in Corneal Epithelium

A method was reported in which sulfate ion labeled with radioisotope ($[^{35}S]$) is incorporated into the tissue, mucin-containing protein is fractionated and the amount of mucin is evaluated based on the amount of mucin-containing protein (*J. Biol. Chem.*, 257, 4709–4718 (1982); and *Am. J. Physiol.*, 244, C391–C398(1983)).

Following the method mentioned in those literatures, the influence of gefarnate on production and secretion of mucin from corneal epithelium was studied, using a method wherein cornea of rats as shown below was used and secreted mucin-containing protein was fractionated by means of dolichosmamerectin (hereinafter, abbreviated as DBA).

(Method of Experiment)

Corneal pieces of 3 mm diameter (five to six pieces per group) were isolated from cornea of male Sprague-Dawley strain rats and incubated in a culture medium (TC-199) for six hours at 37° C. in the presence of 5% of $CO_2$. Then, to the medium was added $[^{35}S]$ sodium sulfate and incubation was further conducted for 18 hours so that $[^{35}S]$ sulfate ion was fully incorporated into the corneal pieces. The medium was removed, the tissue was washed with a phosphate-buffered physiological saline solution. To the tissues were added culture mediums containing various concentrations of gefarnate, respectively, and incubation was conducted for 30 minutes. Then, to the mediums were added gel immobilized with DBA and the mixture was shaken at room temperature for one hour. After shaking, the gel was recovered and the radioactivity of mucin-containing protein which contained $[^{35}S]$ sulfate ion bonded to the gel was measured with a liquid scintillation counter.

(Results)

As an example of the results of the experiment, Table 1 shows the radioactivity of $[^{35}S]$ sulfate ion per wet weight of cornea when the gefarnate concentrations in the medium were 0.01 and 0.1 mg/ml. Incidentally the data in the table are the values calculated when the radioactivity of $[^{35}S]$ sulfate ion per wet weight of cornea without the test compound was defined as 100.

TABLE 1

| Concentration of Gefarnate in Medium | Radioactivity |
|---|---|
| 0.01 mg/ml | 133 |
| 0.1 mg/ml | 166 |

It is apparent from Table 1 that radioactivity of mucin-containing protein which contains $[^{35}S]$ sulfate ion bonded to gel by addition of gefarnate increased and that action for promoting secretion of the mucin-containing protein was noted. Degree of said action was dependent upon the concentration of gefarnate.

From the above result, now it is clear that gefarnate has an excellent promoting action on production and secretion of mucin from corneal epithelium.

2. Production and Secretion of Mucin in Bulbar Conjunctiva

A method was reported in which an impression cytology, which is a kind of biopsy of an organism surface where invasiveness is little and repeated operations are possible by the use of cellulose acetate filter paper, was conducted to confirm the state of conjunctiva by various staining methods (*Ophthalmol.*, 92, 728–733(1985); and *Journal of the Eye*, 11, 1163–1167(1994)).

Now, an impression cytology according to the method mentioned in those literatures was conducted to measure the numbers of goblet cells stained with periodic acid-Schiff (hereinafter abbreviated as PAS) whereby the influence of gefarnate on production and secretion of mucin in bulbar conjunctiva was studied.

(Method of Experiment)

A gefarnate ophthalmic solution was instilled into both eyes of male Japanese white rabbits six times a day during one week. On the next day of the final instillation, cellulose acetate filter paper which had been cut in a size of 3×3 mm was placed on the nasal side bulbar conjunctiva of generally anesthetized rabbit and lightly pressed down for several seconds. Subsequently, this filter paper was removed from the conjunctiva, immersed in a 1:1:20 mixture of 37% formaldehyde, acetic acid and 70% ethanol, and dehydrated with ethanol. This was then immersed in a 0.5% periodic acid and stained with a Schiff reagent. The filter paper was dehydrated with ethanol, then immersed in xylene and embedded in a slide. The goblet cells stained with PAS were observed under a light microscope and their pictures were taken.

(Results)

As an example of the results of the experiment, Table 2 shows the numbers of goblet cells per $mm^2$ in the groups to which the formulation 1 (ophthalmic solution of gefarnate) (gefarnate concentration: 0.1% (w/v)) and the formulation 3 (the same) (gefarnate concentration: 1% (w/v)) were applied. It also shows the numbers of goblet cells per $mm^2$ in the control group to which no opthalmic solution was applied.

TABLE 2

| | |
|---|---|
| Group of no instillation | 194 cells |
| Group of formulation 1 instillation | 192 cells |
| Group of formulation 3 instillation | 274 cells |

It is apparent from Table 2 that instillation of the formulation 3 increased the goblet cell density on bulbar conjunctiva whereby an effect of increasing the cell number was noted.

From this, it is now clear that gefarnate increases the number of goblet cells containing mucin in bulbar conjunctiva and exhibits an excellent promoting action on production and secretion of mucin in bulbar conjunctiva.

It was found from the results of the above pharmacological tests that gefarnate promotes the production and secretion of mucin in cornea and conjunctiva and is useful as a therapeutic agent for dry eye and other keratoconjunctiva diseases such as keratitis, conjunctivitis, corneal erosion and corneal ulcer.

Industrial Applicability

The present invention relates to a therapeutic agent for keratoconjunctiva diseases containing gefarnate as an active ingredient. The therapeutic agent for keratoconjunctiva diseases according to the present invention is applicable to dry eye, keratitis, conjunctivitis, corneal erosion, corneal ulcer, etc.

We claim:

1. A therapeutic agent for keratoconjunctiva diseases containing gefarnate as an active ingredient together with an ophthalmic carrier.

2. The therapeutic agent for keratoconjunctiva diseases according to claim 1 in which the keratoconjunctiva disease is dry eye, keratitis, conjunctivitis, corneal erosion or corneal ulcer.

3. The therapeutic agent for keratoconjunctiva diseases according to claim 1 in which the keratoconjunctiva disease is dry eye.

4. The therapeutic agent for keratoconjunctiva diseases according to claim 1 in the form of an ophthalmic solution.

5. The therapeutic agent for keratoconjunctiva diseases according to claim 4 in which a concentration of gefarnate is 0.1–3% (w/v).

6. The therapeutic agent for keratoconjunctiva diseases according to claim 2 in the form of an ophthalmic solution.

7. The therapeutic agent for keratoconjunctiva diseases according to claim 3 in the form of an ophthalmic solution.

8. The therapeutic agent for keratoconjunctiva diseases according to claim 6 in which a concentration of gefarnate is 0.1–3% (w/v).

9. The therapeutic agent for keratoconjunctiva diseases according to claim 7 in which a concentration of gefarnate is 0.1–3% (w/v).

10. A method for treating a keratoconjunctiva disease comprising administering an effective amount of gefarnate to an eye suffering from the keratoconjunctiva disease.

11. The method of claim 10 wherein said keratoconjunctiva disease is dry eye, keratitis, conjunctivitis, corneal erosion or corneal ulcer, and wherein said gefarnate is administered in the form of an ophthalmic solution containing gefarnate in an amount of 0.01–5% (w/v) or in the form of an ophthalmic ointment.

12. The method according to claim 11 wherein said gefarnate is in the form of an ophthalmic solution and in an amount of 0.1–3% (w/v/).

13. The method according to claim 10 wherein said keratoconjunctiva disease is dry eye.

14. The method according to claim 11 wherein said keratoconjunctiva disease is dry eye.

* * * * *